(12) United States Patent
Sawanobori et al.

(10) Patent No.: US 10,542,957 B2
(45) Date of Patent: Jan. 28, 2020

(54) X-RAY COMPUTED TOMOGRAPHY APPARATUS AND GANTRY APPARATUS

(71) Applicant: Toshiba Medical Systems Corporation, Otawara-shi (JP)

(72) Inventors: Tadashi Sawanobori, Nasushiobara (JP); Yanji Sun, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 211 days.

(21) Appl. No.: 15/854,335

(22) Filed: Dec. 26, 2017

(65) Prior Publication Data

US 2018/0177477 A1 Jun. 28, 2018

(30) Foreign Application Priority Data

Dec. 26, 2016 (JP) .................................. 2016-251023
Dec. 22, 2017 (JP) .................................. 2017-246013

(51) Int. Cl.
  *A61B 6/00* (2006.01)
  *A61B 6/03* (2006.01)
  *A61B 6/04* (2006.01)

(52) U.S. Cl.
  CPC .............. *A61B 6/54* (2013.01); *A61B 6/032* (2013.01); *A61B 6/0407* (2013.01); *A61B 6/4435* (2013.01); *A61B 6/5205* (2013.01)

(58) Field of Classification Search
  CPC ........... A61B 6/032; A61B 6/035; A61B 6/54; A61B 6/0407; A61B 6/4435; A61B 6/5205
  See application file for complete search history.

(56) References Cited

U.S. PATENT DOCUMENTS

| 2010/0177867 A1 | 7/2010 | Kozelj et al. |
| 2015/0196367 A1* | 7/2015 | Muller .................. A61B 6/032 |
| | | 600/410 |

FOREIGN PATENT DOCUMENTS

| JP | 2010-500118 | 1/2010 |
| JP | 2011-254888 | 12/2011 |

* cited by examiner

*Primary Examiner* — Courtney D Thomas
(74) *Attorney, Agent, or Firm* — Oblon, McClelland, Maier & Neustadt, L.L.P.

(57) ABSTRACT

According to embodiment, an x-ray computed tomography apparatus includes a gantry apparatus. The gantry apparatus includes a housing, at least one light projector, and a transmission film. The housing has a bore through which an object is inserted, and a scan mechanism for x-ray CT imaging. The light projector is provided inside the housing and configured to emit a visible light beam. The transmission film is attached to an inner wall of the housing that faces the bore, and allows the visible light beam emitted from the light projector to pass through. The transmission film has a color in a wavelength band that allows the visible light beam to pass through, and reduces the visibility of the inside of the housing from the outside, where the wavelength band excludes a wavelength of a color of the visible light beam.

13 Claims, 5 Drawing Sheets

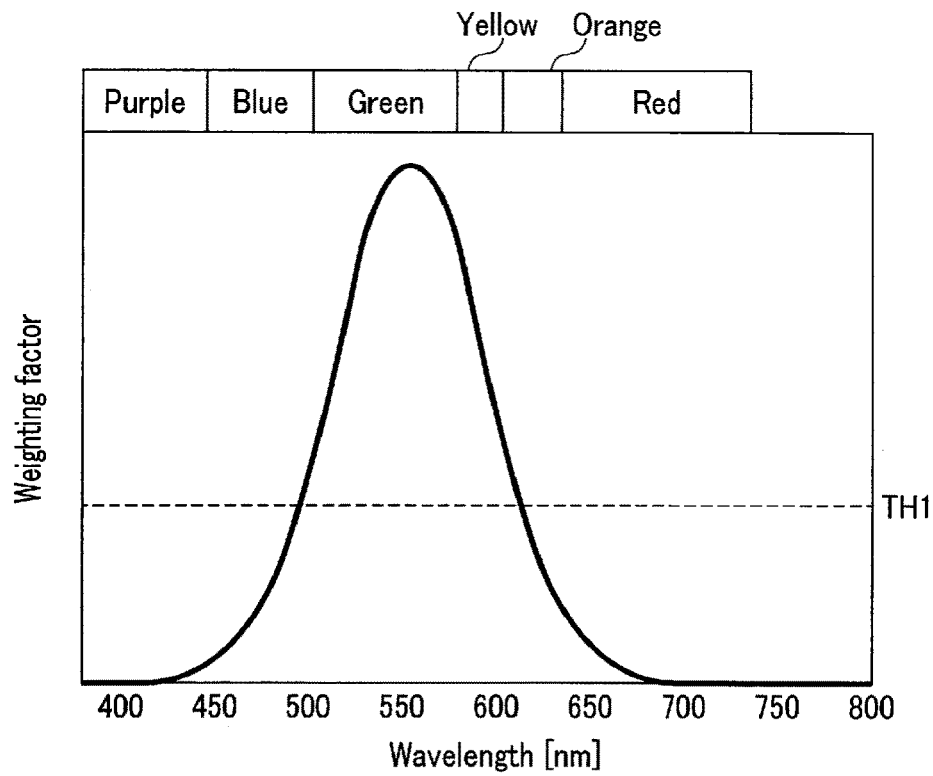
F I G. 4
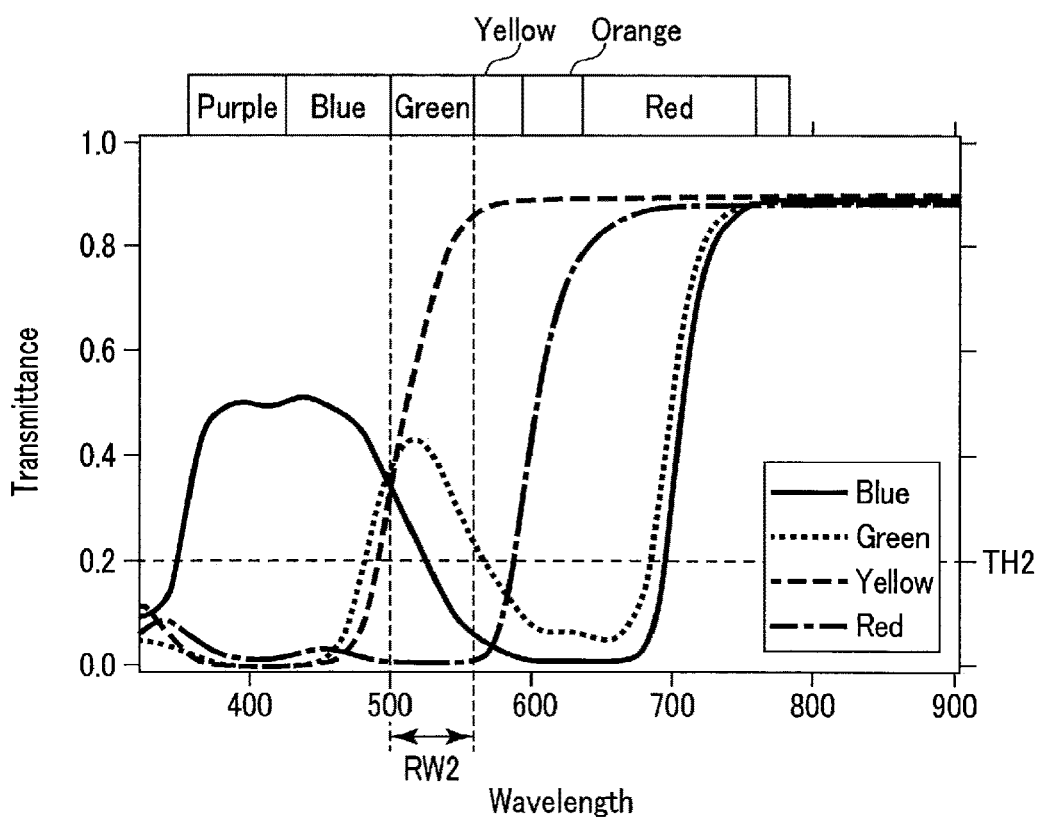
F I G. 5

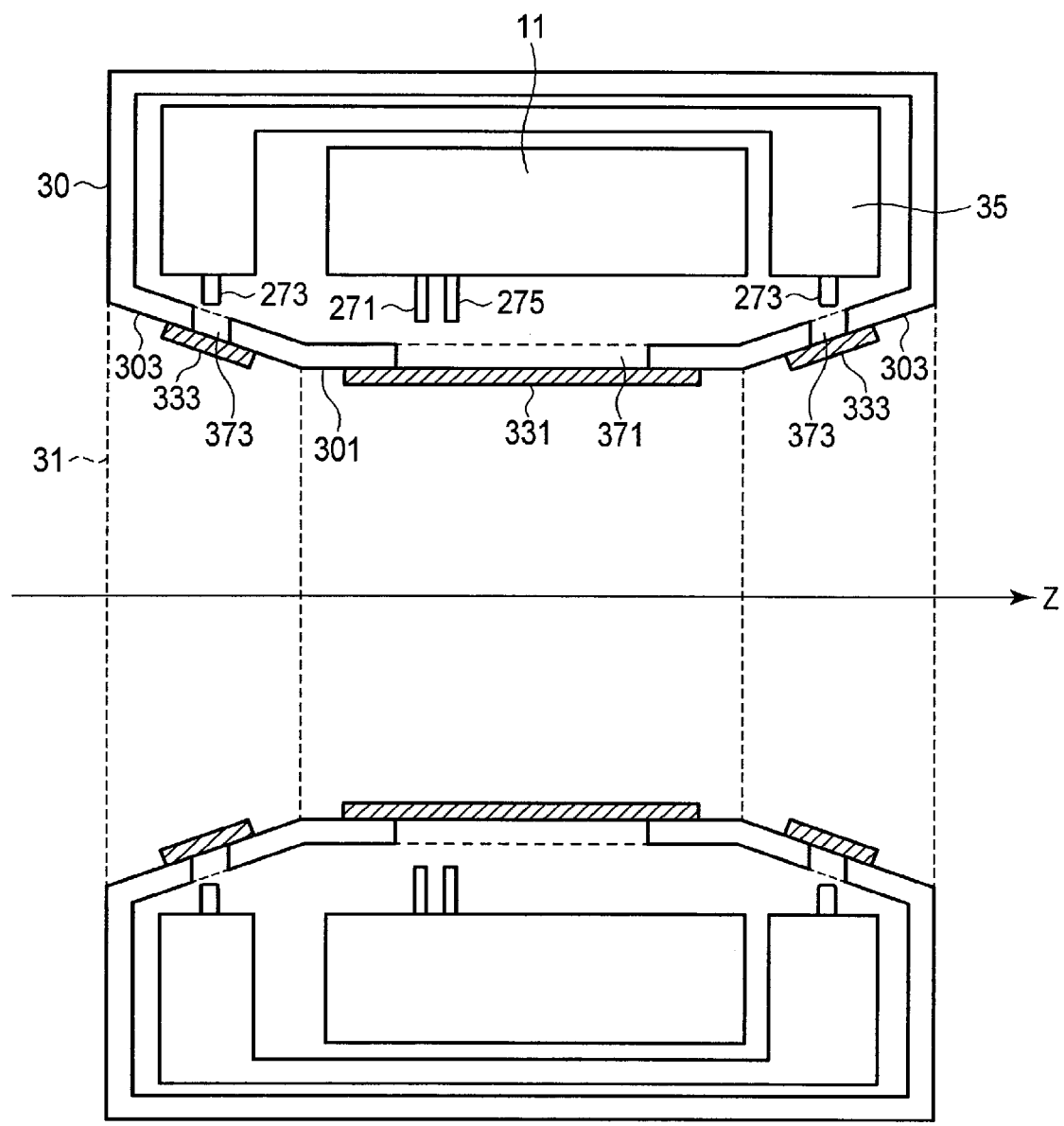
F I G. 6

X-RAY COMPUTED TOMOGRAPHY APPARATUS AND GANTRY APPARATUS

CROSS-REFERENCE TO RELATED APPLICATIONS

This application is based upon and claims the benefit of priority from the Japanese Patent Application No. 2016-251023, filed Dec. 26, 2016 and the Japanese Patent Application No. 2017-246013, filed Dec. 22, 2017, the entire contents of both of which are incorporated herein by reference.

FIELD

Embodiments described herein relate generally to an x-ray computed tomography apparatus and a gantry apparatus.

BACKGROUND

In an x-ray computed tomography apparatus, a gantry apparatus is provided with a light projector therein for positioning of a patient. A visible light beam emitted from the light projector passes through a transmission film provided in the housing of the gantry apparatus and is incident on the patient and the bed. In general, such a transmission film is formed as a transparent or translucent film, and therefore the inside of the gantry housing may be visible through the film to the patient who is lying on the bed. If the inside of the gantry housing is visible during x-ray CT imaging, the eyes of the patient tend to follow a rotation unit that is rotating inside the gantry housing at high speed. This may cause the head of the patient to move, which may result in body motion artifacts.

BRIEF DESCRIPTION OF THE DRAWING

FIG. 4 is a chart presenting the wavelength distribution of the weighting factors of transmittance demonstrated by different colors for the transmission films illustrated in FIGS. 2 and 3.

FIG. 5 is a chart presenting the wavelength distribution of transmittance (transmission spectrum) demonstrated by different colors for the transmission films of FIGS. 2 and 3.

FIG. 6 is a cross-section of a gantry that includes the z-axis, according to a modification example of the present embodiment.

DETAILED DESCRIPTION

An x-ray computed tomography apparatus according to the embodiment includes a gantry apparatus that conducts x-ray CT imaging, and a processing apparatus that controls the gantry apparatus. The gantry apparatus includes a gantry housing, at least one light projector, and a transmission film. The gantry housing is provided with a bore, through which an object enters, and includes a scan mechanism for the x-ray CT imaging. The light projector is provided inside the gantry housing to emit a visible light beam. The transmission film is provided on the inner wall of the gantry housing that faces the bore, and allows the visible light beam emitted from the light projector to pass through. The transmission film has a color that belongs to a wavelength band which allows the visible light beam to pass through and which makes it difficult to see the inside of the gantry housing from the outside (i.e. from the viewpoint of the patient lying on the bed). The wavelength band for the color of this transmission film excludes the wavelength of the visible light beam.

Figure 1:
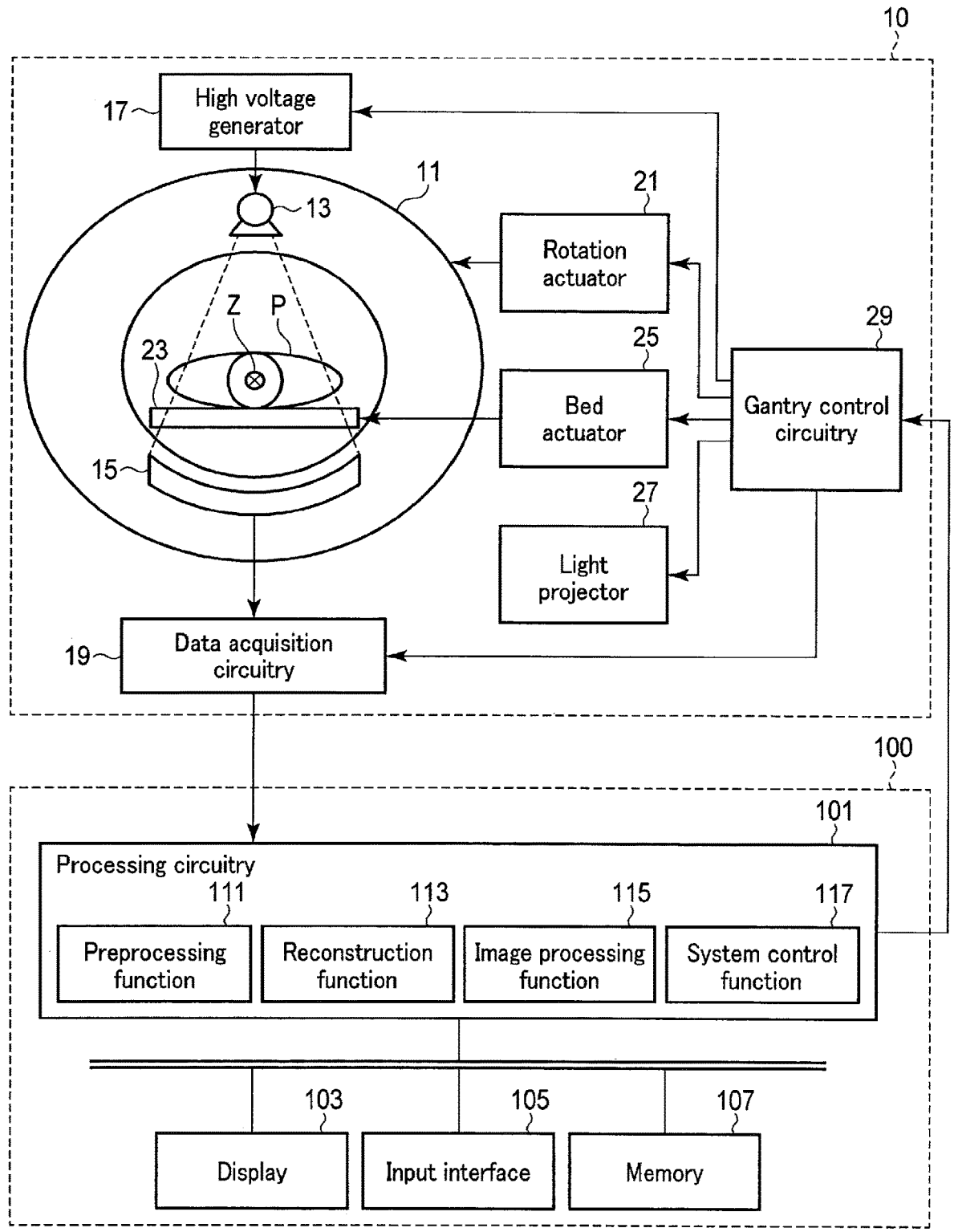
FIG. 1 is a diagram showing the structure of an x-ray computed tomography apparatus according to the present embodiment.

FIG. 1 is a diagram showing the structure of the x-ray computed tomography apparatus according to the present embodiment. As illustrated in FIG. 1, the x-ray computed tomography apparatus according to the present embodiment includes a gantry 10 and a console 100. The gantry 10 may be installed in a CT examination room, and the console 100 may be installed in a control room adjacent to the CT examination room. The gantry 10 and the console 100 are connected to each other in a communicable manner. A scan mechanism is mounted on the gantry 10 to perform CT imaging on an object P by x-rays. The console 100 is a computer that controls the gantry 10.

As illustrated in FIG. 1, the gantry 10 has a cylindrical rotation frame 11 with a bore provided therein. The rotation frame 11 may also be referred to as a rotation unit. As shown in FIG. 1, the rotation frame 11 is provided with an x-ray tube 13 and x-ray detector 15 to oppose each other across the bore. The rotation frame 11 is an annular-shaped metal frame, formed of a metal such as aluminum. The gantry 10 also has a main frame formed of a metal such as aluminum, which will be described later. The main frame may also be referred to as a fixation unit. The rotation frame 11 is rotatably supported by this main frame.

The x-ray tube 13 generates x-rays. The x-ray tube 13 includes a cathode that generates thermoelectrons, an anode that receives the thermoelectrons emitted from the cathode and thereby produces x-rays, and a vacuum tube that holds the cathode and anode therein. The x-ray tube 13 is connected to a high voltage generator 17 by way of a high voltage cable. The high voltage generator 17 may be attached to the rotation frame 11. With the control by a gantry control circuitry 29, the high voltage generator 17 generates a high voltage to be applied to the x-ray tube 13 and supplies a filament heating current. The high voltage is applied between the anode and cathode contained in the x-ray tube 13, and the filament heating current is supplied to the cathode of the x-ray tube 13. The high voltage applied between the anode and cathode of the x-ray tube 13 is referred to as a tube voltage. Under this high voltage, thermoelectrons generated from the cathode that has been heated by the filament heating current are emitted to the anode. This flow of thermoelectrons is referred to as a tube current. The high voltage generator 17 adjusts the tube voltage and the tube current to the x-ray tube 13 in accordance with x-ray conditions.

The rotation frame 11 receives power from a rotation actuator 21 and rotates around the central axis Z with constant angular speed. As the rotation actuator 21, any motor, such as a direct drive motor or servomotor, can be used. The rotation actuator 21 may be contained in the gantry 10. Upon receipt of a drive signal from the gantry control circuitry 29, the rotation actuator 21 generates power to rotate the rotation frame 11.

An FOV is defined in the bore of the rotation frame 11. A top panel supported by a bed 23 is inserted in the bore of the rotation frame 11. The object P is positioned on this top panel. The bed 23 movably supports the top panel, and contains a bed actuator 25. Upon receipt of a drive signal from the gantry control circuitry 29, the bed actuator 25 generates power to move the top plate back and forth, up and down, and left and right. The bed 23 moves the top panel for positioning so that the imaging target area of the object P can fit in the FOV.

The x-ray detector 15 detects the x-rays emitted from the x-ray tube 13. In particular, the x-ray detector 15 includes a plurality of detection elements that are aligned on a two-dimensional curved surface. Each of the detection elements has a scintillator and a photoelectric conversion element. The scintillator is formed by a material which can convert x-rays to light, and converts the incident x-rays to photons, the number of which is determined in accordance with the intensity of the incident x-rays. The photoelectric conversion element is a circuit element that amplifies the light received from the scintillator and converts it to electric signals. As a photoelectric conversion element, a photomultiplier tube or photodiode may be adopted. The detection element may be an indirect detection type, which first converts the x-rays to light in order to detect the x-ray, as described above. Alternatively, the element may be a direct detection type, which directly converts the x-rays to electric signals.

Data acquisition circuitry 19 is connected to the x-ray detector 15. In accordance with the instructions from the gantry control circuitry 29, the data acquisition circuitry 19 reads from the x-ray detector 15 the electric signals which correspond to the intensity of the x-rays detected by the x-ray detector 15. Based on the read-out electric signals, the data acquisition circuitry 19 collects raw data that includes a digital value corresponding to the dose of x-rays for a view time. The data acquisition circuitry 19 may be realized by an Application Specific Integrated Circuit (ASIC) that contains a circuit element designed to generate raw data.

In accordance with the instructions from the gantry control circuitry 29, the light projector 27 projects a visible light beam (laser projection) onto the top panel inserted into the bore, or onto the object P positioned on the top panel. The visible light beam emitted from the light projector 27 may be red, green, blue, or in any other color. This visible light beam is projected for the positioning of the object P.

In order to execute the x-ray CT imaging in accordance with the imaging conditions received from the preprocessing circuitry 101 of the console 100, the gantry control circuitry 29 controls the high voltage generator 17, the data acquisition circuitry 19, the rotation actuator 21, and the bed actuator 25 in a synchronous manner. As hardware resources, the gantry control circuitry 29 may include a processing apparatus (processor) such as a Central Processing Unit (CPU) or a Micro Processing Unit (MPU), and a storage apparatus (memory) such as a Read Only Memory (ROM) or a Random Access Memory (RAM). The gantry control circuitry 29 may be realized by an ASIC, Field Programmable Gate Array (FPGA), any other Complex Programmable Logic Devices (CPLD), or Simple Programmable Logic Device (SPLD).

As illustrated in FIG. 1, the console 100 includes the processing circuitry 101, a display 103, an input interface 105, and a memory 107. Data communications between the preprocessing circuitry 101, the display 103, the input interface 105 and the memory 107 are conducted via a bus.

The preprocessing circuitry 101 includes, as a hardware resource, a processor such as a CPU, MPU, or Graphics Processing Unit (GPU). The preprocessing circuitry 101 implements various programs and thereby realizes a preprocessing function 111, reconstruction function 113, image processing function 115, and system control function 117.

With the preprocessing function 111, the preprocessing circuitry 101 executes preprocessing such as logarithmic transformation onto the raw data sent from the gantry 10. The raw data that has been subjected to this preprocessing may be referred to as projection data.

With the reconstruction function 113, the preprocessing circuitry 101 generates a CT image that represents the spatial distribution of CT values for the object P, based on the preprocessed raw data. As an image reconstruction algorithm, a known algorithm, such as filtered back projection (FBP) and successive approximation reconstruction, may be used.

With the image processing function 115, the preprocessing circuitry 101 implements various image processing onto the CT image that has been reconstructed with the reconstruction function 113. For example, the preprocessing circuitry 101 may implement three-dimensional image processing onto the CT image, such as volume rendering, surface volume rendering, image value projection processing, Multi-Planer Reconstruction (MPR) processing, and Curved MPR (CPR) processing, to generate a display image.

With the system control function 117, the preprocessing circuitry 101 performs overall control over the x-ray computed tomography apparatus according to the present embodiment. In particular, the preprocessing circuitry 101 reads and starts up the control programs stored in the memory 107, and controls the components of the x-ray computed tomography apparatus in accordance with the started control programs.

The preprocessing function 111, reconstruction function 113, image processing function 115 and system control function 117 may be implemented on a single substrate of the preprocessing circuitry 101, or may be implemented separately on multiple substrates of the preprocessing circuitry 101.

The display 103 displays the CT images and various types of information such as scan plans. In particular, the display 103 is connected to the display interface that is provided in the console 100. The display interface converts the data representing the display target to video signals. These video signals are supplied to the display 103, and the display 103 displays video signals representing the display target. As the display 103, a CRT display, liquid crystal display, organic EL display, LED display, plasma display, or any other display known in this field of technology may be suitably chosen and used. The display 103 may be provided on the gantry 10, or on the wall of the CT examination room. The display 103 may be a motion picture projector.

The input interface 105 is connected to an input device. The input device receives various instructions from a user. As the input device, a keyboard, a mouse, and switches may be used. The input interface 105 supplies output signals received from the input device, to the preprocessing circuitry 101 via a bus.

The memory 107 is a storage device, such as a Read Only Memory (ROM), Random access memory (RAM), Hard Disk Drive (HDD), Solid State Drive (SSD), and integrated-circuit storage device, for storing various types of information. The memory 107 may store CT images and scan plans. Alternatively, as a hardware component, the memory 107 may be a drive unit that can read various information from, and write it to, a portable storage medium such as a CD-ROM drive, DVD drive, and flash memory.

Figure 2:
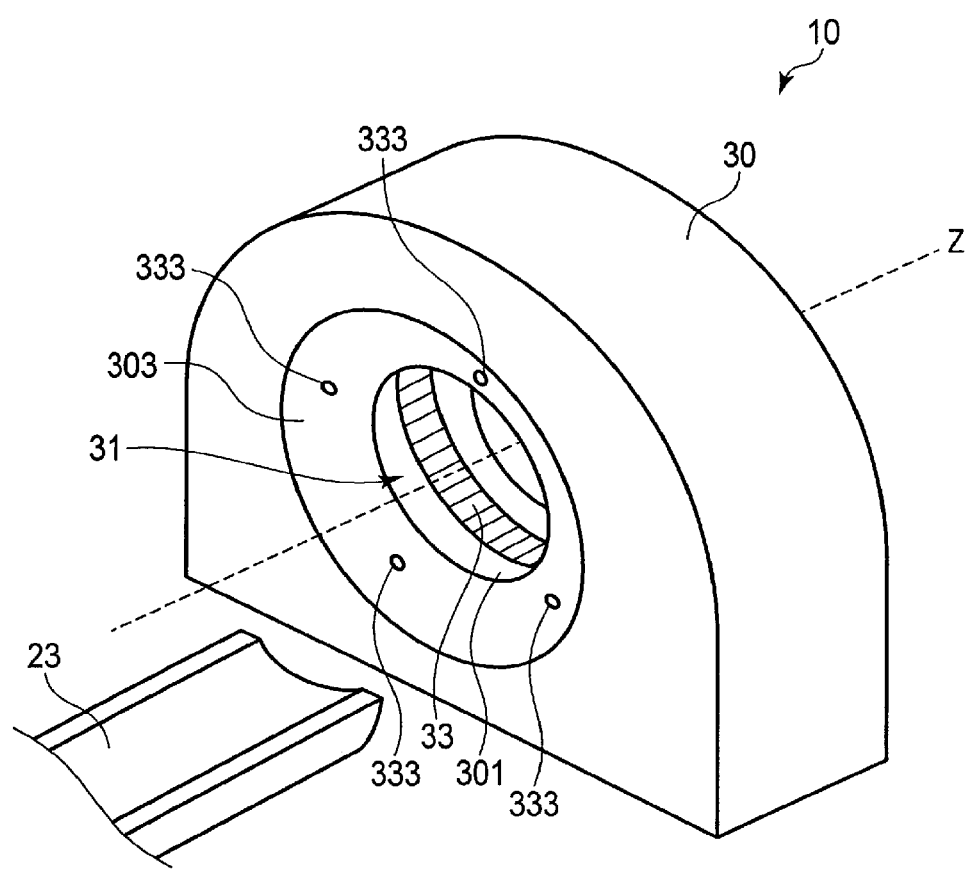
FIG. 2 is a diagram showing the outer appearance of a gantry according to the present embodiment.
Figure 3:
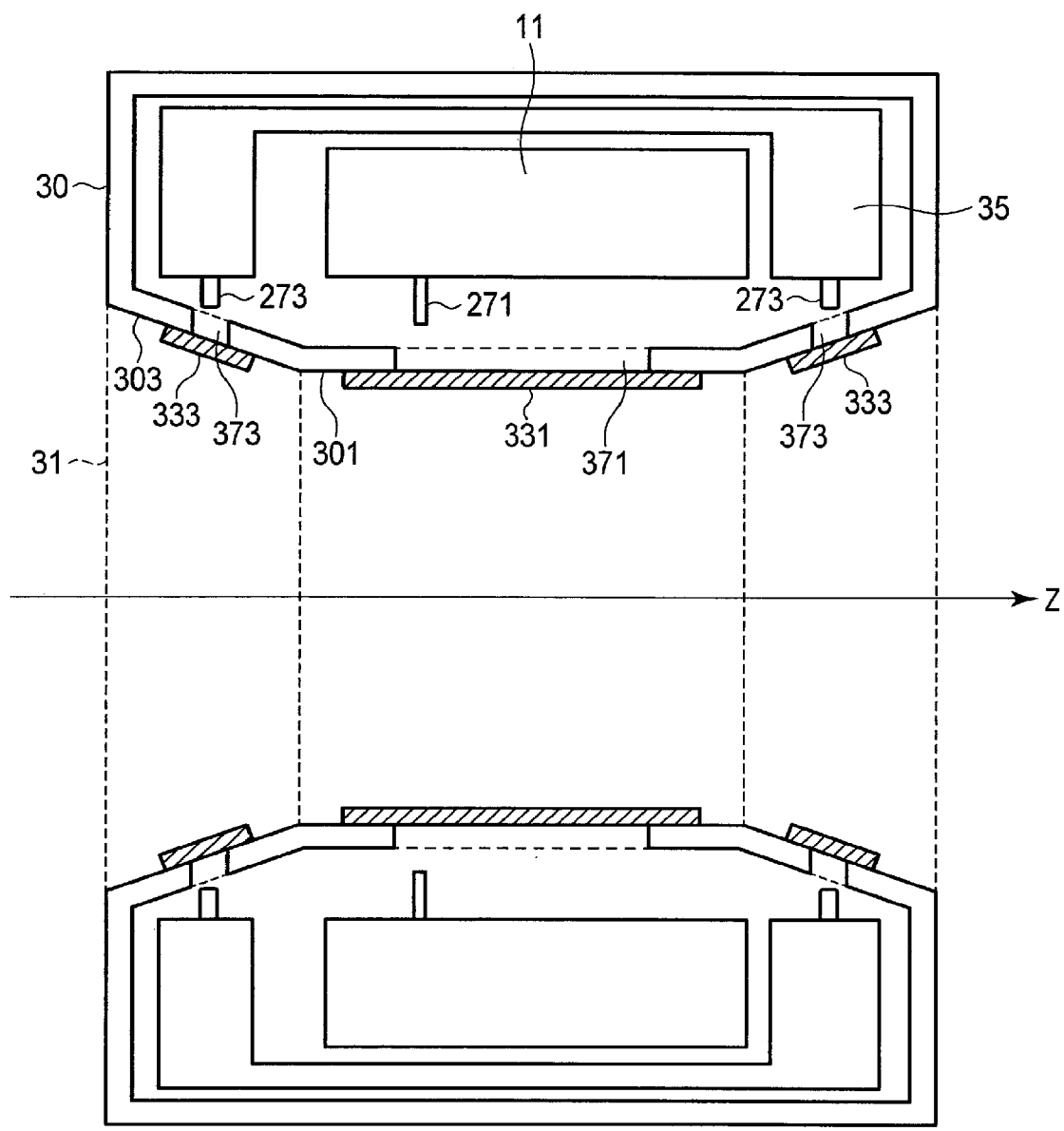
FIG. 3 is a cross section of the gantry of FIG. 2 that includes the z-axis.

FIG. 2 is a diagram showing the outer appearance of the gantry 10 according to the present embodiment. FIG. 3 is a cross section of the gantry 10 of FIG. 2 that includes the z-axis. As illustrated in FIGS. 2 and 3, the gantry 10 has a substantially cylindrical gantry housing 30 in which a bore 31 is provided. The gantry housing 30 contains a main frame 35, which serves as a fixation unit, and a rotation frame 11, which serves as a rotation unit. The main frame 35 supports the rotation frame 11, with a bearing interposed therebetween, in such a manner as to be continuously rotatable around the z-axis. An x-ray tube 13, an x-ray detector 15 and data acquisition circuitry 19, which are not shown, are provided in the rotation frame 11. A light projector (hereinafter, referred to as an inner light projector) 271 is attached to the rotation frame 11 in such a manner that a visible light beam can be emitted toward the bore 31. The inner light projector 271 projects a visible light beam which makes the reference lines of the imaging range, or the entire imaging range, directly visible. Another light projector (hereinafter, referred to as an outer light projector) 273 is also attached to the main frame 35 so that a visible light can be emitted toward the bore 31. The outer light projector 273 projects a visible light beam which makes the reference lines of the imaging range directly visible. The inner light projector 271 and outer light projector 273 will be referred to simply as light projectors 27, where they need not be differentiated from each other.

FIGS. 2 and 3 show a structure in which two inner light projectors 271 are attached to the rotation frame 11, but the x-ray computed tomography apparatus according to the present embodiment is not limited thereto. The number of inner light projectors 271 attached to the rotation frame 11 may be arbitrarily determined. Similarly, the number of outer light projectors 273 attached to the main frame 35 is not limited to four, but may be arbitrarily determined.

In FIGS. 2 and 3, transmission films 33 are provided on the inner walls 301 and 303 of the gantry housing 30, which face the bore 31. The beveled inner wall 303 is referred to as a peripheral inner wall, and the remaining inner wall is referred to as a central inner wall. The beveling is provided to ease a feeling of entrapment in the bore 31.

The central inner wall 301 is provided with a slit 371 through which the visible light beam emitted from the inner light projector 271 and the x-ray generated by the not-shown x-ray tube 13 can pass. In consideration of the rotation frame 11 to which the inner light projector 271 and x-ray tube 13 are attached, the slit 371 is provided in the central inner wall 301 in its entire circumferential length around the z-axis. A transmission film (hereinafter referred to as a center transmission film) 331 is deposited to cover the slit 371. In other words, the visible light beam projected from the inner light projector 271 and the x-ray generated by the x-ray tube 13 pass through the center transmission film 331.

The peripheral inner wall 303 is provided with holes 373 through which the visible light beam emitted from the outer light projectors 273 pass. The holes 373 are formed only in the emission directions of the visible light beams of the outer light projectors 273. Transmission films (hereinafter referred to as peripheral transmission films) 333 are deposited to cover the holes 373. The center transmission film 331 and peripheral transmission films 333 will be referred to simply as transmission films 33 when they need not be differentiated from each other. The visible light beams projected from the outer light projectors 273 and the x-ray generated by the x-ray tube 13 pass through the peripheral transmission films 333. That is, the visible light beam projected from the inner light projector 271 and the visible light beams projected from the outer light projectors 273 pass through different transmission films 33.

The transmission film 33 should be in a color that belongs to a wavelength band which allows the visible light beams from the light projectors 27 to pass through and which also makes the inside of the gantry housing 30 difficult to see from the outside, where the wavelength of the color of the visible light beam should be excluded from this wavelength band. Particularly, as the wavelength band that makes the inside of the gantry housing 30 difficult to see from the outside, the wavelength band that can screen the inside of the gantry housing 30 from the outside may be used. As long as the center transmission film 331 allows the visible light beam from the inner light projector 271 to pass through and the peripheral transmission film 333 allows the visible light beam from the outer light projector 273 to pass through, the center transmission film 331 and the peripheral transmission film 333 may be in the same color or in different colors. The inner light projector 271 and outer light projector 273 may emit visible light beams of the same color or of different colors. The transmission film 33 may be formed of any material as long as the above conditions can be satisfied. For example, the transmission film 33 may be formed of a polyester film such as Mylar (Trademark).

The method for determining the color of the transmission film 33 is now discussed in detail.

According to the present embodiment, the color is defined by its wavelength. For convenience of description, the wavelength bands are defined as follows: a wavelength band from 380 to 450 nm is purple, a wavelength band from 450 to 500 nm is blue, a wavelength band from 500 to 570 nm is green, a wavelength band from 570 to 590 nm is yellow, a wavelength band from 590 to 620 nm is orange, a wavelength band from 620 to 750 nm is red. The wavelength bands of colors are not limited to the above, but any wavelength may be defined as corresponding to any color.

Predominantly, a red beam is adopted as a visible light beam to be projected by light projectors of x-ray computed tomography apparatuses. Although green and blue demonstrate higher visibility to human eyes than red, few x-ray computed tomography apparatuses have adopted green and blue light emission. This is because a light projector that projects a green or blue visible light beam is expensive and unable to withstand large centrifugal force caused by the rotation of the rotation frame 11. With the advancement of technology, however, the use of light projectors that can project green or blue visible light beams is expected to increase. The embodiment discussed below focuses on the determination of a color of the transmission film 33 with respect to the light projector 27 that projects a green visible light beam.

The color of the transmission film 33 is determined based on the wavelength distribution of the weighting factor of the transmittance demonstrated by the possible colors for the transmission film 33, and the wavelength distribution of the transmittance (transmission spectrum) demonstrated by the possible colors for the transmission film 33.

FIG. 4 is a chart presenting the wavelength distribution of the weighting factor of the transmittance demonstrated by possible colors for the transmission film 33. The vertical axis of the chart in FIG. 4 is defined by the weighting factor, and the horizontal axis is defined by the wavelength [nm]. The weighting factor is determined in accordance with the luminosity function in order to calculate the transmittance of a visible light beam. The color that has a wavelength with the greater weighting factor is more transmissive to light beams of any colors. As indicated in FIG. 4, the weighting factor peaks in the wavelength band of green, and lowers as the wavelength is away from the peak wavelength. In other words, green is the color that allows the light beams of any colors to pass through most easily.

A typical gantry that uses a red visible light beam adopts a transmission film 33 of the same color, i.e., red. Suppose, for a gantry that uses a green visible light beam, a transmission film 33 of the same color, i.e., green is chosen in a similar manner. Green is a color that allows light of any color to pass through, and therefore the inside of the gantry housing 30 will be easy to see from the outside. Thus, as a color of the transmission film 33, a color that belongs to a wavelength band other than that of green should be used. In particular, colors in wavelength bands having a weighting factor lower than or equal to the weighting factor threshold TH1 can be choices for the color of the transmission film 33. Colors in the wavelength bands having a weighting factor lower than or equal to the threshold TH1 may include purple, blue, orange, and red.

FIG. 5 is a chart indicating the wavelength distribution of transmittance (transmission spectrum) for different colors possible for the transmission film 33. The vertical axis of the chart in FIG. 5 is defined by the transmittance, and the horizontal axis is defined by the wavelength [nm]. The solid line represents a blue transmission film 33, the dotted line represents a green transmission film 33, the broken line represents a yellow transmission film 33, and the dashed-dotted line represents a red transmission film 33. As can be seen from FIG. 5, the wavelength distribution of the transmittance differs in accordance with the color of the transmission film 33. In general, the transmittance of the yellow and red films stays low with regard to the light of any wavelength band lower than the wavelength band of the film's own color; the transmittance sharply increases in the vicinity of the wavelength band of the own color, and stays high in the wavelength band higher than the wavelength band of the own color. For the blue and green films, their transmittance peaks at the medium level in the vicinity of the wavelength band of the own color, and sharply increases in the vicinity of the wavelength band of red, and stays high in the wavelength band higher than the wavelength band of red.

Specifically, as presented in FIG. 5, the transmittance of the yellow film stays approximately at the low level of 0.1 between 350 nm and 450 nm, sharply increases at about 450 nm, and stays at a high level of 0.8 after about 450 nm. The transmittance of the red film stays at the low level of 0.1 between 350 nm and about 650 nm, sharply increases at around 650 nm, and stays at a high level of 0.8 after around 650 nm. The transmittance of the blue film gradually increases from 0.1 between 350 and 380 nm, stays at a relatively high level of 0.5 between 380 and 450 nm, decreases down to 0.1 between 450 and 600 nm, and stays at a low level of 0.1 between 600 and 700 nm; the transmittance then sharply increases at around 700 nm and stays at a high level of 0.8 after 700 nm. The transmittance of the green film stays at a low level of 0.1 between 350 and 480 nm, increases to 0.4 between 450 and 520 nm, decreases down to 0.1 between 520 and 600 nm, and stays around 0.1 between 600 and 700 nm; the transmittance then sharply increases at around 700 nm, and stays at a high level of 0.8 after around 700 nm.

As shown in FIG. 5, when the transmission film 33 is blue, it demonstrates the transmittance of 0.3 in the wavelength band for green, which means that the blue film allows a green visible light beam to partially pass through. When the transmission film 33 is green, it demonstrates the transmittance of 0.4 in the wavelength band for green, which means that the green film allows a green visible light beam to partially pass through. When the transmission film 33 is yellow, it demonstrates the transmittance of 0.7 in the wavelength band for green, which means that the yellow film allows for excellent transmission of a green visible light beam. When the transmission film 33 is red, it demonstrates the transmittance of 0.1 in the wavelength band for green, which means that the red film scarcely allows a green visible light beam to pass through. The wavelength distribution of transmittance of orange is the wavelength distribution of transmittance of red combined with the wavelength distribution of transmittance of yellow. Based on this, the transmission film 33 that is orange will demonstrate the transmittance of 0.3 in the wavelength band for green. This means that the orange film allows a green visible light beam to partially pass through. The wavelength distribution of transmittance of purple is the wavelength distribution of transmittance of red combined with the wavelength distribution of transmittance of blue. Based on this, the transmission film 33 that is purple will demonstrate the transmittance of 0.2. This means that the purple film allows a green visible light beam to partially pass through.

In particular, when possible colors are selected for the transmission film 33 from the aspect of its transmittance, a transmittance threshold TH2 is determined in the wavelength distribution of transmittance. For the light projector 27 that emits a green visible light beam, colors that demonstrate a transmittance higher than or equal to the threshold TH2 in the wavelength band RW2 to which green belongs. For the light projector 27 that emits a green visible light beam, the threshold TH2 may be set to 0.2. By referring to this threshold, purple, blue, green, orange, and yellow can be chosen as possible colors for the transmission film 33.

As discussed above, when the light projector 27 emits a green visible light beam, purple, blue, orange, and red are chosen as the color choices for the transmission film 33 from the aspect of the weighting factor. On the other hand, from the aspect of the transmittance, purple, blue, green, orange, and yellow are chosen as the color choices for the transmission film 33. In view of this, for the light projector 27 whose visible light beam is green, the color of the transmission film 33 should be chosen from purple, blue, and orange, which are in the wavelength bands that are not the wavelength band of the color of the visible light beam, i.e., green.

When, for example, the inner light projector 271 that emits a green visible light beam is used, the selected color of the center transmission film 331 may be purple, blue, or orange. With such a choice, the center transmission film 331 allows the green visible light beam emitted from the inner light projector 271 to pass through, while it reduces the visibility of the inside of the gantry housing 30 from the outside. With the center transmission film 331 that allows for excellent transmission of the green visible light beam from the inner light projector 271, the user can readily perform the positioning of the patient P using the inner light projector 271. Furthermore, because the visibility of the inside of the gantry housing 30 from the outside can be reduced, the eyes of the patient P will not intentionally or unintentionally follow the rotation frame 11, which will prevent the movement of the head of the patient. As a result, motion artifacts can be reduced.

The color of the peripheral transmission film 333 can be determined in a manner similarly to the center transmission film 331. That is, the color of the peripheral transmission film 333 may be chosen from the colors in the wavelength bands that allow the visible light beam emitted from the outer light projector 273 to pass through while screening the inside of the gantry housing 30 from the outside. Such wavelength bands should not include the wavelength band to which the color of the visible light beam belongs. When the visible light beam of the outer light projector 273 is green, the selected color of the peripheral transmission film 333 may be purple, blue, or orange. In this manner, the peripheral transmission film 333 allows the green visible light beam emitted from the outer light projector 273 to pass through, and at the same time, reduces the visibility of the inside of the gantry housing 30.

The above method for determining the color of the transmission film 33 is not limited to the visible light beam of the light projector 27 being green; it is equally applicable to visible light beams of blue, red or any other colors. As indicated in FIGS. 4 and 5, when the visible light beam is blue, the color of the transmission film 33 may be chosen from blue and purple. When the visible light beam is red, the color of the transmission film 33 may be chosen from red, orange, and purple. If the color of the transmission film 33 is determined to be in a wavelength band to which the wavelength of the color of the visible light beam does not belong, purple may be chosen for the color of the transmission film 33 with respect to a blue visible light beam, and orange or purple may be chosen for the transmission film 33 with respect to a red visible light beam.

The color of the visible light beam of the inner light projector 271 may be different from the color of the visible light beam of the outer light projector 273. For example, the visible light beam of the inner light projector 271 may be green, and the visible light beam of the outer light projector 273 may be red. If this is the case, the color of the center transmission film 331 is selected from purple, blue, and orange, and the color of the peripheral transmission film 333 is selected from red, orange, and purple, as discussed above. In this manner, the visible light beam of the inner light projector 271 and the visible light beam of the outer light projector 273 both become clearly discernible, while the visibility of the inside of the gantry housing 30 can be reduced. By allowing the inner light projector 271 and the outer light projector 273 to use different colors for their visible light beams, mixing of the beams from the inner light projector 271 and from the outer light projector 273 can be avoided.

Modification Example

According to the above embodiment, visible light beams that pass through a single transmission film 33 are of the same color, but the embodiment is not limited thereto. For example, the visible light beams that pass through the center transmission film 331 do not have to be limited to the same color; they may be of two, three, or more colors. Such a modification example of the present embodiment will be explained below. In this explanation, structural elements having the same or similar functions will be denoted by the same reference symbols, and a repetitive description will be given only where necessary.

FIG. 6 is a cross-section of the gantry 10 that includes the z-axis, according to a modification example of the present embodiment. As illustrated in FIG. 6, the gantry 10 according to the modification example is provided with two inner light projectors 271 and 275 on the rotation frame 11. The inner light projector 271 projects a visible light beam in order to make the reference lines of the imaging area directly viewable. The inner light projector 275 projects a visible light beam in order to make the entire imaging range directly viewable. The visible light beam of the inner light projector 271 and the visible light beam of the inner light projector 275 pass through the same center transmission film 331.

The color of the transmission film 331 should be selected so that the visible light beam of the inner light projector 271 and the visible light beam of the inner light projector 275 can both pass through the film, while the visibility of the inside of the gantry housing 30 from the outside can be reduced. For instance, the inner light projector 271 may be of a type that projects a red visible light beam, and the inner light projector 275 may be of a type that projects a green visible light beam. The method for determining the color of the center transmission film 331 according to the modification example will be explained.

Based on the wavelength distribution of the weighting factor in FIG. 4, purple, blue, orange, and red are chosen as the possible colors for the center transmission film 331. Based on the wavelength distribution of the transmittance in FIG. 5, with respect to a red visible light beam, the possible colors of the center transmission film 331 may be purple, blue, green, yellow, orange, and red, and with respect to a green visible light beam, the possible colors of the center transmission film 331 may be purple, blue, orange, and red. Based on FIGS. 4 and 5, purple, blue, orange, and red are chosen as the possible colors for the center transmission film 331. Thus, when a projector of a type that emits a red visible light beam is adopted as the inner light projector 271, and a projector of a type that emits a green visible light beam is adopted as the inner light projector 275, the color of the center transmission film 331 is determined from purple, blue, orange, and red. If the color of the center transmission film 331 is determined to be in a wavelength band that does not include the wavelengths of the colors of the visible light beams of the inner light projector 271 and inner light projector 275, the color of the center transmission film 331 is determined from purple, blue and orange. The center transmission film 331 allows the red visible light beam emitted from the inner light projector 271 and the green visible light beam emitted from the inner light projector 275 to suitably pass through, and therefore the user can readily perform the positioning of the patient P using the inner light projector 271 and the inner light projector 275. In addition, the visibility of the inside of the gantry housing 30 from the outside can be reduced so that the eyes of the patient P will not intentionally or unintentionally follow the rotation frame 11, which could cause the movement of the head of the patient. Thus, motion artifacts can be reduced. Furthermore, because of the inner light projector 271 and the inner light projector 275 emitting visible light beams of different colors, any confusion of the inner light projector 271 and the inner light projector 275 can be avoided by these colors.

According to the present embodiment, the gantry 10 is used for an x-ray computed tomography apparatus, but the embodiment is not limited thereto. The gantry, as long as it is provided with light projectors 27 and transmission films 33, is applicable to any medical imaging diagnostic apparatus that performs medical diagnosis based on the imaging principle, such as magnetic resonance imaging apparatus and nuclear medicine diagnostic apparatus.

According to at least one embodiment as explained above, the visibility of a visible light beam emitted from a light projector can be maintained, while the visibility of the inside of the gantry housing can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An x-ray computed tomography apparatus, comprising a gantry apparatus that performs x-ray CT imaging, and a processing apparatus that controls the gantry apparatus, wherein
the gantry apparatus comprises:
a gantry housing that has a bore through which an object is inserted, and a scan mechanism for x-ray CT imaging;
at least one light projector that is provided in the gantry housing and configured to emit a visible light beam; and
a transmission film that is attached to an inner wall of the gantry housing that faces the bore, and allows the visible light beam emitted from the light projector to pass through,
the transmission film has a color in a wavelength band that allows the visible light beam to pass through and reduces visibility of inside of the gantry housing from outside, the wavelength band excluding a wavelength of a color of the visible light beam.

2. The x-ray computed tomography apparatus according to claim 1, wherein the transmission film is determined based on a wavelength distribution of weighting factors of transmittance with respect to possible colors for the transmission film and a wavelength distribution of transmittance with respect to the possible colors of the transmission film.

3. The x-ray computed tomography apparatus according to claim 2, wherein the transmission film has a color that belongs to a wavelength band having a weighting factor smaller than or equal to a first value and having a transmittance greater than or equal to a second value with respect to the visible light beam.

4. The x-ray computed tomography apparatus according to claim 1, wherein
the visible light beam is green, and
the transmission film is orange, blue, or purple.

5. The x-ray computed tomography apparatus according to claim 1, wherein
the visible light beam is blue, and
the transmission film is orange or purple.

6. The x-ray computed tomography apparatus according to claim 1, wherein
the at least one light projector comprises a first light projector that emits a first visible light beam of a first color that passes through the transmission film, and a second light projector that emits a second visible light beam of a second color that is different from the first color and that passes through the transmission film, and
the transmission film has a color in a wavelength band that allows both the first visible light beam and the second visible light beam to pass through, and reduces the visibility of the inside of the gantry housing from the outside.

7. The x-ray computed tomography apparatus according to claim 6, wherein
the first color is a color selected from a group of red, green, and blue,
the second color is a color selected from a group of red, green, and blue, and is different from the first color, and
the color of the transmission film is orange or purple.

8. The x-ray computed tomography apparatus according to claim 6, further comprising:

a rotation frame provided inside the gantry housing, and having an x-ray tube and an x-ray detector arranged across the bore from each other; and
a main frame provided inside the gantry housing, and supporting the rotation frame rotatably around a central axis of the bore,
wherein the first light projector and the second light projector are provided on the rotation frame.

9. The x-ray computed tomography apparatus according to claim 1, wherein the wavelength band that reduces the visibility of the inside of the gantry housing from the outside is a wavelength band with which the inside of the gantry housing can be screened from the outside.

10. The x-ray computed tomography apparatus according to claim 1, wherein
the light projector comprises a first light projector that is provided inside the gantry housing and emits a first visible light beam of a first color, and a second light projector that is provided in the gantry housing and emits a second visible light beam of a second color that is different from the first color,
the transmission film comprises a first transmission film that is attached to an inner wall of the gantry housing that faces the bore and allows the first visible light beam emitted from the first light projector to pass through, and a second transmission film that is attached to the inner wall and allows the second visible light beam emitted from the second light projector to pass through,
the first transmission film has a color in a wavelength band that allows the first visible light beam to pass through, and reduces the visibility of the inside of the gantry housing from the outside, the wavelength band excluding a wavelength of the first color of the first visible light beam, and
the second transmission film has a color in a wavelength band that allows the second visible light beam to pass through, and reduces the visibility of the inside of the gantry housing from the outside, the wavelength band excluding a wavelength of the second color of the second visible light beam.

11. The x-ray computed tomography apparatus according to claim 10, further comprising:
a rotation frame provided inside the gantry housing, and having an x-ray tube and an x-ray detector arranged across the bore from each other; and
a main frame provided inside the gantry housing, and supporting the rotation frame rotatably around a central axis of the bore,
wherein the first light projector and the second light projector are provided on the rotation frame.

12. The x-ray computed tomography apparatus according to claim 10, further comprising:
a rotation frame provided inside the gantry housing, and having an x-ray tube and an x-ray detector arranged across the bore from each other; and
a main frame provided in the gantry housing, and supporting the rotation frame rotatably around a central axis of the bore,
wherein the first light projector is provided on the rotation frame, and
the second light projector is provided on the main frame.

13. A gantry apparatus comprising:
a gantry housing that has a bore through which an object is inserted, and a scan mechanism for medical imaging;

at least one light projector provided inside the gantry housing and configured to emit a visible light beam; and a transmission film that is attached to an inner wall of the gantry housing that faces the bore, and allows the visible light beam emitted from the light projector to pass through, wherein the transmission film has a color in a wavelength band that allows the visible light beam to pass through and reduces visibility of inside of the gantry housing from outside, the wavelength band excluding a wavelength of a color of the visible light beam.

* * * * *